(12) United States Patent
Deroberts

(10) Patent No.: US 8,784,462 B2
(45) Date of Patent: Jul. 22, 2014

(54) FLEXIBLE, WEARABLE THERAPEUTIC LASER ARRAY

(71) Applicant: Richard Ogden Deroberts, Wardensville, WV (US)

(72) Inventor: Richard Ogden Deroberts, Wardensville, WV (US)

( * ) Notice: Subject to any disclaimer, the term of this patent is extended or adjusted under 35 U.S.C. 154(b) by 0 days.

(21) Appl. No.: 13/690,706

(22) Filed: Nov. 30, 2012

(65) Prior Publication Data
US 2014/0155962 A1    Jun. 5, 2014

(51) Int. Cl.
*A61N 5/06*    (2006.01)

(52) U.S. Cl.
CPC .......................................... *A61N 5/06* (2013.01)
USPC ..................................... 607/89; 606/9; 607/88

(58) Field of Classification Search
None
See application file for complete search history.

(56) References Cited

U.S. PATENT DOCUMENTS

| | | | |
|---|---|---|---|
| 5,505,726 A * | 4/1996 | Meserol | 606/9 |
| 6,045,575 A * | 4/2000 | Rosen et al. | 607/88 |
| 6,134,475 A * | 10/2000 | Will | 607/98 |
| 6,221,095 B1 * | 4/2001 | Van Zuylen et al. | 607/88 |
| 6,273,904 B1 * | 8/2001 | Chen et al. | 607/88 |
| 2008/0071255 A1 * | 3/2008 | Barthe et al. | 606/9 |

* cited by examiner

*Primary Examiner* — Lynsey Crandall

(57) ABSTRACT

Method of producing a therapeutic laser device (TLD). The TLD includes stretchable, flexible membranes which comprise a high pressure air cavity. High air pressure is produced by fans which are speed controllable by computer. Standoff posts provide, an attachment function, and a separation function between the TLD and the patient. Semiconductor laser diodes and lens sets in a two dimensional array produce the therapeutic laser light. Cooling air tubes direct air controlled by temperature sensors from the high pressure cavity onto laser diodes. Capacitive proximity sensors in conjunction with infrared radiation sensors confirm close contact with a patient and allow lasing. Power is supplied either by battery or by connection to mains power. A touch screen computerized device with wireless communication displays information to the user and controls the therapy session. The TLD and the power supply both have stretchable straps enabling the TLD to be fixed to the patient.

14 Claims, 12 Drawing Sheets

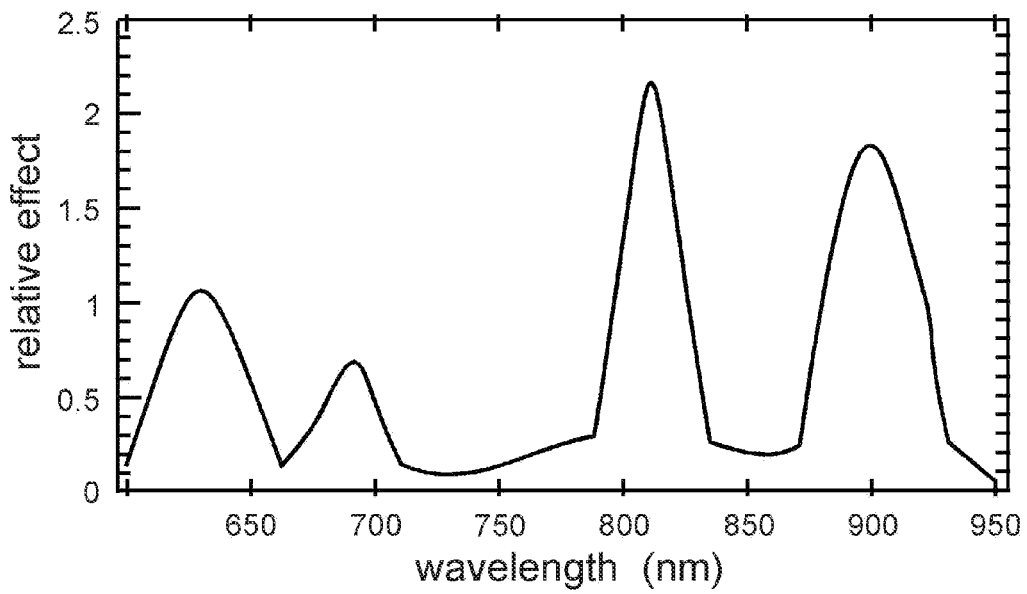

Generalized action spectrum for LLLT effects in cells, animals and patients. Data shown are an amalgamation of many literature reports from multiple laboratories.

An action spectrum is the rate of a physiological activity plotted against wavelength of light. It shows which wavelength of light is most effectively used in a specific chemical reaction.

Mechanisms of Low Level Light Therapy.

Michael R. Hamblin and Tatiana N. Demidova.

Wellman Center for Photomedicine, Massachusetts General Hospital.

Department of Dermatology, Harvard Medical School.

Harvard-MIT Division of Health Sciences and Technology.

Sackler School of Graduate Biomedical Sciences,

Tufts University School of Medicine.

Proc. of SPIE Vol. 6140 Art. No. 614001-9

FIG. 17

FLEXIBLE, WEARABLE THERAPEUTIC LASER ARRAY

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING A TABLE, OR A COMPUTER PROGRAM LISTING COMPACT DISC APPENDIX

Not Applicable

BACKGROUND OF THE INVENTION

1. Technical Field of Invention

Embodiments in accordance with the invention relate generally to phototherapy. Phototherapy is a therapeutic physical modality using photons from the visible and infrared spectrum for tissue wound and burn healing, pain reduction, rhytide reduction (skin wrinkle) and hair follicle growth. It has also been shown to induce adipose cell membrane pore creation thereby allowing triglycerides, glycerol and free fatty acids to transit across the membrane into interstitial space. There have been more than 4000 studies published worldwide on the benefits of low level laser therapy (LLLT) and the effects observed with therapeutic lasers. Photo-biomodulation increases ATP synthesis by changing the oxidation/reduction status of the mitochondria and activates the sodium/potassium pump thereby altering cell membrane permeability to calcium. Cell growth has been stimulated by an increase in cell metabolism. Higher levels of cell regeneration have been documented. LLLT has been shown to stimulate nerve function and the production of nitric oxide and endorphins. The neuropeptide substance P (SP) and histamine have been shown to be reduced thereby reducing local inflammatory response. LLLT also reduces the formation of acetylcholine, and bradikynin. LLLT has also been shown to reduce fibrous tissue formation. In photodynamic therapy (PDT) a photosensitizer is mixed with antibodies that are targeted to antigens on abnormal tissue. This mixture is then administered to the patient and binds with the antigens. Radio magnetic radiation having a wavelength corresponding to the absorption wavelength of the photosensitizer is then administered to the patient. This treatment reduces the size of the abnormal tissue.

2. Description of Related Art

Low level laser therapeutic instruments (LLLTI) achieve their therapeutic effect by emitting laser radiation at a chosen frequency or frequencies at a chosen power level for a chosen period of time at a chosen distance over a chosen area. Generally laser power is measured in watts, area is measured in centimeters (cm) squared, distance is measured in centimeters and time is measured in seconds. Therapeutic dosage is measured in watts multiplied by seconds divided by area in cm squared. Watts multiplied by seconds is defined as joules so dosage then is joules/cm squared. From this we see that to apply the larger dosage to the same area we can either increase the power of the laser or the length of time the laser light is applied, or both. Small hand held LLLTI require more time for the treatment of a given area because they must be moved repeatedly. However, small hand held laser instruments are useful for treating areas which are curved or have small hollows. Larger LLLTI with many more lasers cover a greater area but require cumbersome cooling apparatus to keep the lasers from overheating. Because most large LLLTI are not flexible they do not apply an even and precise dosage to any part of the treatment area which is curved or contains small hollows. In the case of both small LLLTI and most large area LLLTI patients are required to remain still, (seated or lying), while the treatment is applied. This is so because the instruments are held in place by either the patient's or technician's hand or laid onto the patient in a horizontal manner and kept in place by gravity. In the case of scanning LLLTI the laser beam is spread over a large area and requires a high power laser applied for a long period of time to administer the same dosage. Scanning LLLTI do not apply an even and precise dosage pattern because the laser diode is not a constant distance from the entire treatment area and because a scan line contains more laser energy in the center of the scan line than at either of the ends of the scan line. None of the LLLTI designs discussed above are easily transported and none of them can be used by a patient while performing typical household or office functions. Generally LLLTI require connection to mains power at the wall and have control systems which are floor standing. This limits the ability of a patient to move about or in most cases even sit up.

Several newer LLLTI designs have the ability to conform to the contours of a patient's body but are problematic for several reasons. These LLLTI position the lasers in contact with the patient's skin or very close to the skin. This positioning concentrates the laser beam in a small diameter at the center of the treatment area because the beam does not have room to expand over the entire treatment area. Some designs employ vertical cavity surface emitting lasers (VCSEL) or horizontal cavity surface emitting lasers (HCSEL) devices. These lasers project a very narrow beam with almost no beam divergence and cannot spread their light energy over the entire treatment area without optical lenses which these LLLTI do not employ. In addition these designs are made of non-breathable materials held in direct contact with the skin. In some cases these LLLTI are intended to be worn for many hours at a time and in some cases days at a time. This can cause skin rashes, be extremely uncomfortable, retard blood flow in the area, and cause sweating which can attenuate the laser light. Some of these LLLTI are programmed to energize at specific time intervals during the day and night. If the LLLTI has been removed by the patient in order to bathe or because of discomfort the LLLTI will not recognize this and run its programmed course of treatment without the patient being involved.

All LLLTI designs discussed above are problematic for eye safety. Laser light can damage the eye very quickly even at low power levels. Laser light in the visible spectrum is obvious to operator and patient and can be avoided with care. Laser light in the infrared spectrum is problematic because it is not obvious and does not cause pain until great damage has been done.

All semiconductor lasers produce heat when energized. Edge emitting lasers produce more heat than VCSEL or HCSEL devices because they are less efficient. Heat causes lasers to reduce their laser power output and to shift their laser light frequency to longer wavelengths. Referring to FIG. 17 of the drawings it is shown that physiological activity affected by laser light energy is not uniform but is greater in certain wavelengths than others. Also it is shown that by changing the frequency only slightly the effect of the laser light can be reduced by 80% or more. This reduction of the laser affect combined with the reduction of power output of the laser caused by rising temperature can render the LLLTI completely ineffective. Automatic power control systems which monitor the laser power output and try to maintain a constant power output exacerbate the problem by increasing the electrical energy supplied to the laser diode thereby further increasing the heat generated. Without cooling laser diodes can 'run away' and burn out immediately or have their life span reduced dramatically. The temperature of a patient's treatment area can vary significantly. The temperature of the hand or foot can be 20 degrees Fahrenheit cooler than the chest. Also room temperature will cause differences in skin temperature. Different body physiques will cause significant differences in skin temperature from one patient to the next. The only way to ensure that the laser diodes are lasing at the optimum frequency is with active temperature control.

BRIEF SUMMARY OF THE INVENTION

A typical embodiment in accordance with the invention provides a method of producing a therapeutic laser device (TLD). The TLD includes a stretchable, flexible membrane. This membrane is bonded to a second narrow closed cell membrane which in turn is bonded to a flexible, non-stretchable membrane. This structure comprises a high pressure air cavity. This structure has bonded to it high pressure fans. The high pressure fans are speed controllable. The fans are regulated by a power supply and computer control coupled to an electrical cable for power and sensor data communication. The flexible, non-stretchable membrane (9) has attached to it a flexible membrane with bonded flat electrical conductors. The flexible, non-stretchable membrane (9) is attached to the flexible membrane with bonded flat electrical conductors by means of standoff posts which penetrate and hold together the two membranes. The standoff posts provide, in addition to their attachment function, a separation function between the TLD and the surface area to be treated on a patient. The flexible membrane with bonded flat electrical conductors has coupled to it semiconductor laser diodes and lens sets and automatic power control circuit electronic modules in a two dimensional array. The flexible membrane with bonded flat electrical conductors is coupled to an electrical cable for power and sensor data communication. The flexible, non-stretchable membrane (9) and the flexible membrane with bonded flat electrical conductors are pierced by cooling air tubes and spacers. The cooling air tubes and spacers direct air from the high pressure cavity onto the emission side of the semiconductor laser diode and lens sets. The cooling air tubes and spacers also provide a spacer function between the stretchable, flexible closed cell membrane and the flexible, non-stretchable membrane. The semiconductor laser diodes and lens sets are comprised of a semiconductor laser diode and a collimating lens and a plano-concave lens. To ensure that radiant laser energy is always disabled when the TLD is not in close contact with a patient's treatment area capacitive proximity sensors in conjunction with infrared radiation sensors transmit data through the electrical cable to the power supply and computer control. The standoff posts and the cooling air tube and spacer are held in place on the emission side of the semiconductor laser diode and lens sets by flexible membrane washers. The temperature of the semiconductor laser diode and lens sets is monitored by temperature sensors and this data is transmitted to the power supply and computer control via the electrical cable. The power supply and computer control can provide power either by battery or by connection to mains power at the wall. The power supply and computer control contains a key lock, a laser radiation full duration indicator light and a laser radiation momentary at start audible signal device. A touch screen computerized device with wireless communication displays information to the user, communicates with the power supply and computer control with wireless communication, initiates a laser therapy session, terminates a laser therapy session, maintains therapy duration timing, displays to the user the elapsed time and the time left in the therapy session, displays to the user battery charge level and prohibits the initiation of a therapy session if battery charge is below a prescribed level, lets a user set therapy duration, lets a user set laser power level, lets the user set the total therapy dosage, calculates the laser power level and therapy duration based on total therapy dosage, lets the user choose between continuous or pulsed laser operation, stores previous therapy session data and lets the user select a previously stored therapy regimen, lets a medical professional transmit a therapy regimen to the touch screen computerized device with wireless communication via the internet or cellular telephone and monitor the status of the TLD and the number of therapy sessions completed, sounds an audible signal when a therapy session is initiated, sounds an audible signal when a therapy session is terminated, waits a standard length of time after the audible signal before powering the lasers, determines the correct positioning of the TLD with respect to the users treatment area using data input from the capacitive proximity sensor and the infrared radiation sensors, terminates a therapy session in the case the TLD becomes separated from the users treatment area and sounds an audible alarm, warns the user of problems encountered by the TLD, shuts the TLD down in the event of malfunction, lets the user pause the therapy session and restart the therapy session, displays a standard laser warning message about laser safety, maintains a constant communication dialog with the power supply and computer control and in the event the communication dialog is broken the power supply and computer control terminates the therapy session. The communication transmission between the computerized device with wireless communication and the power supply and computer control is encrypted for security as is the transmission over the internet or cellular phone. The touch screen computerized device with wireless communication is either a made for purpose device programmed to perform the functions described above and provided with the TLD or it is an application program loadable to a cellphone, touch screen tablet, lap top computer or a desk top computer which has been approved and certified as being capable of performing the stated functions. The TLD and the power supply and computer control both have stretchable straps with hook and loop fasteners. The stretchable straps with hook and loop fasteners enable the TLD to be fixed to the patient in a manner that allows movement of the area to be treated and movement of the patient within and without the treatment premises. The stretchable straps are connected to the TLD with zippers to enable quick removal for cleaning and replacement. The movement of the patient must not exceed the maximum range of the communication capability between the power supply and computer control and the touch screen computerized device or the therapy session will be terminated by the power supply and computer control.

BRIEF DESCRIPTION OF THE SEVERAL VIEWS OF THE DRAWING

FIG. 17 is a graph of Generalized Action Spectrum for LLLT effects in cells, animals and patients.

DETAILED DESCRIPTION OF THE INVENTION

Figure 1:
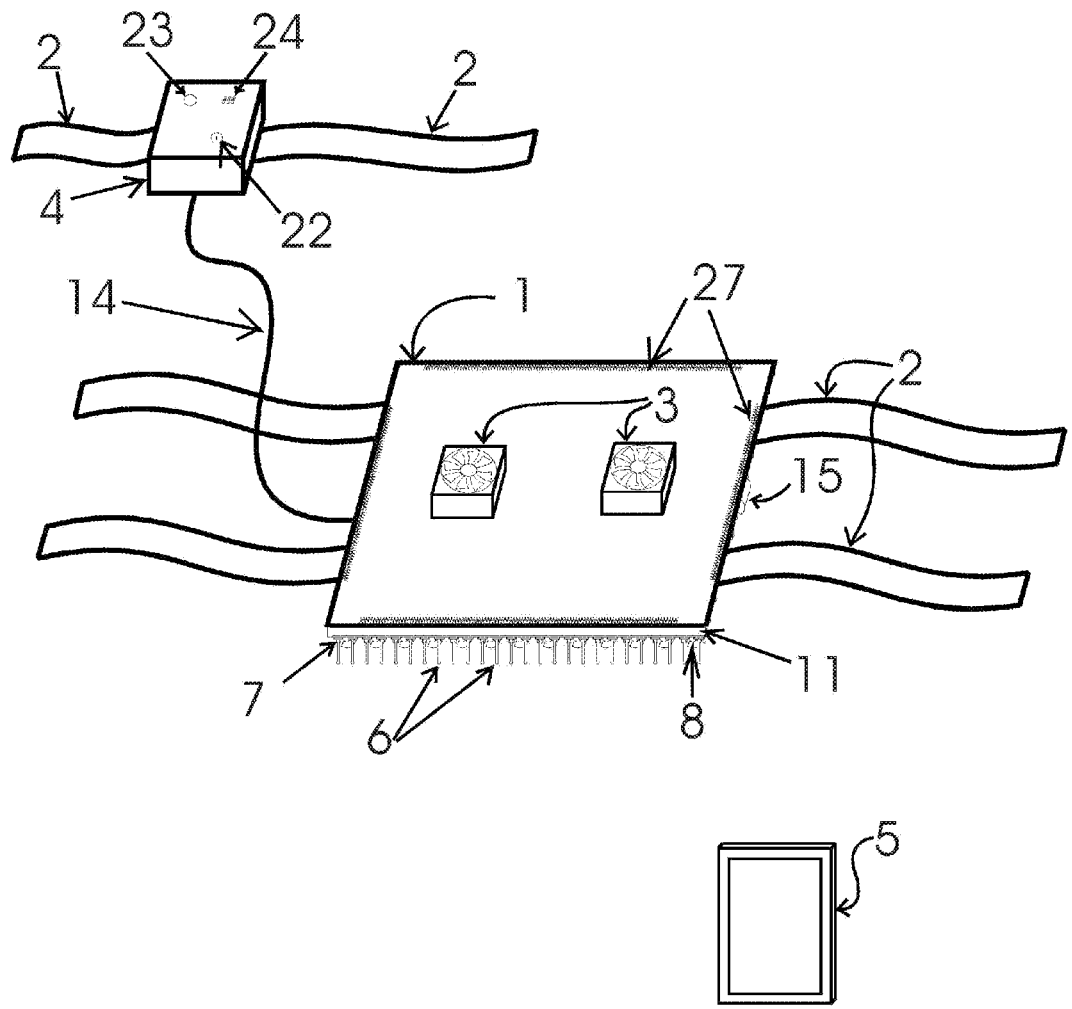
FIG. 1 is a view showing one possible embodiment of the present invention with all the major assemblies depicted in a usable arrangement.

The following references to the drawings are discussed in the narrative below.

1 Stretchable, flexible closed cell membrane
2 Stretchable straps with hook and loop fasteners
3 High pressure fan with speed control and air filter
4 Power supply and computer control with wireless communication
5 Touch screen computerized device with wireless communication
6 Standoff post
7 Semiconductor laser diode and lens set
8 Cooling air tube and spacer
9 Flexible, non-stretchable membrane
10 Flexible membrane with bonded flat braided and/or non-braided electrical conductors
11 Narrow, stretchable, flexible closed cell membrane
12 Flexible membrane washer
13 High pressure air cavity
14 Electrical cable for power and sensor data communication
15 Capacitive proximity sensor
16 Infrared radiation sensor
17 Collimating lens
18 Plano-concave lens
19 Semiconductor laser diode
20 Temperature sensor
21 Automatic power control circuit electronic modules
22 Key lock
23 Laser radiation full duration indicator light
24 Laser radiation momentary at start audible signal device
25 Flat braided and/or non-braided electrical conductors
26 Holes in flexible, non-stretchable membrane
27 Zipper attachment for stretchable straps with hook and loop fasteners The present disclosure relates to producing a therapeutic laser device. Specific examples of membranes, layer configuration, materials, and other arrangements are described below to simplify the present disclosure. These are, of course, merely examples and are not intended to limit the invention from that described in the claims.

Referring now to FIG. 1 of the drawings, the reference numeral (1) refers to a stretchable, flexible closed cell membrane. The term stretchable in this context means the ability to elongate at least 10% of its length without permanently deforming. The term flexible in this context means the ability to bend in an arc with radius of 4 inches or less without permanently deforming. The term closed cell membrane in this context means a material similar to polyethylene foam, neoprene foam, polystyrene foam and others. The membrane (1) has mounted on it one or more high pressure fans with speed control and air filters reference numeral (3), which draw air in from above and force it beneath membrane (1).

Figure 2:
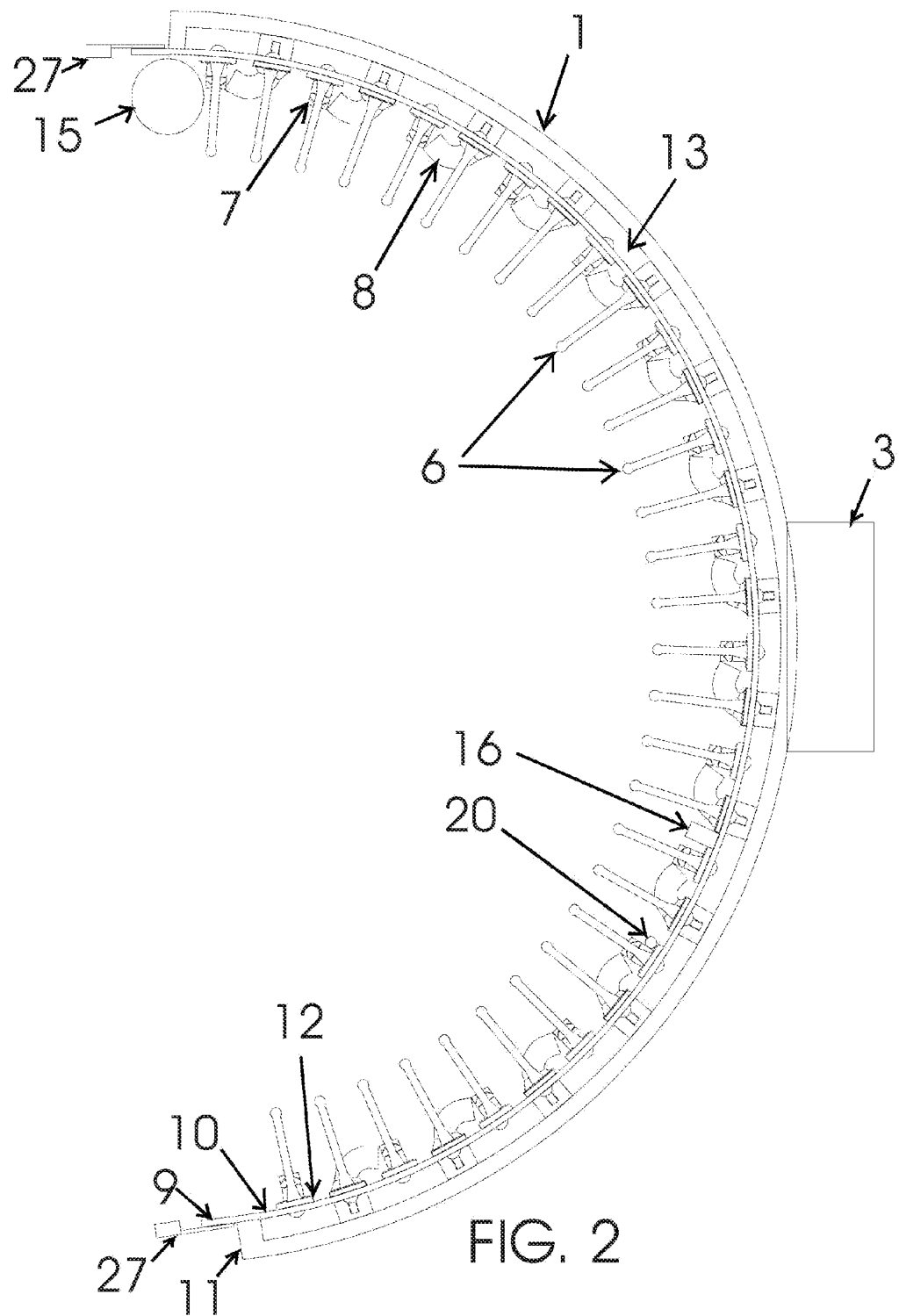
FIG. 2 is a side view of the present invention showing in more detail the sub-assemblies of the TLD in a flexed position.
Figure 3:
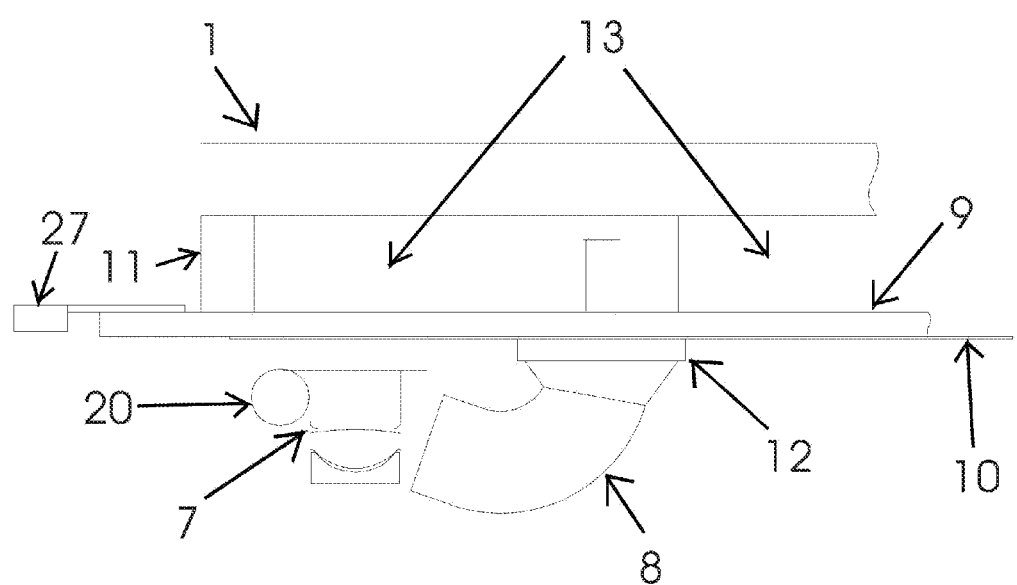
FIG. 3 is a side view of the present invention showing in detail the arrangement of the cooling air tube and spacer in relation to the semiconductor laser diode and lens sets, the high pressure air cavity and the temperature sensors.
Figure 5:
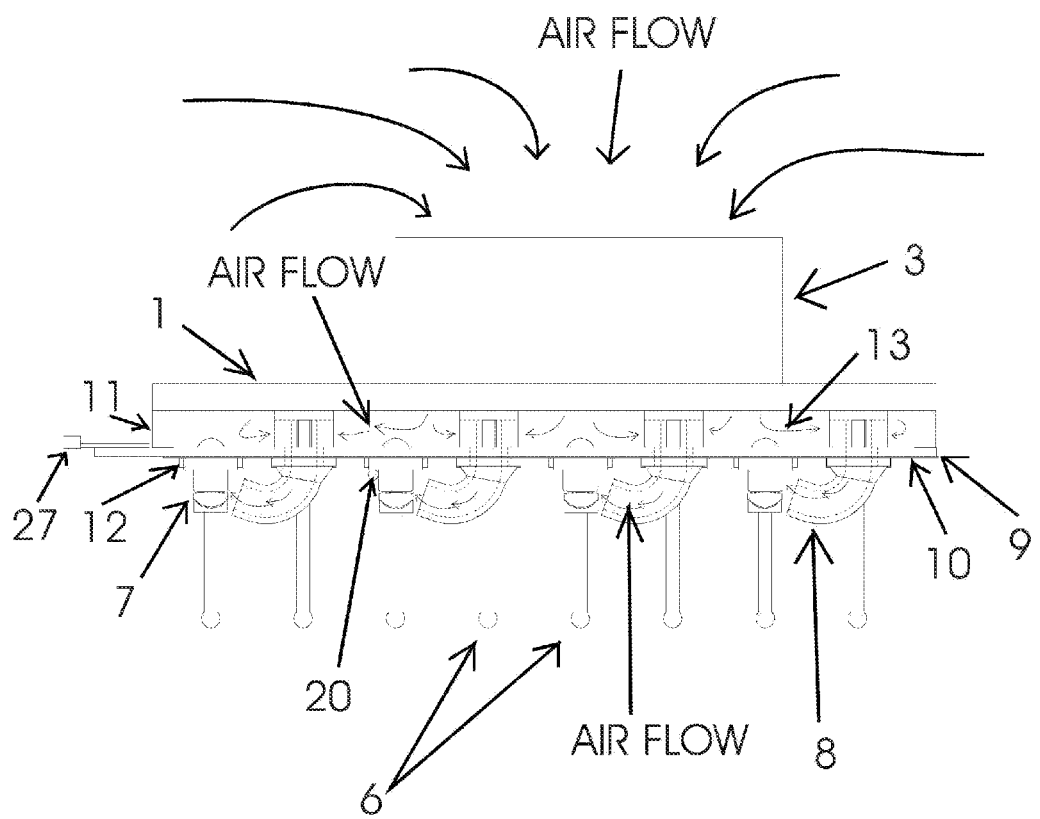
FIG. 5 is a side view of the present invention showing in detail the cooling air flow through the high pressure fan with speed control and air filters, the high pressure air cavity, the cooling air tubes and spacers and onto the semiconductor laser diodes and lens sets.

Referring now to FIG. 2 and FIG. 3 and FIG. 5 of the drawings, the reference numeral (11) refers to a narrow stretchable, flexible closed cell membrane bonded to membrane (1). Reference numeral (9) refers to a flexible, non-stretchable membrane bonded to membrane (11). The term non-stretchable in this context means the inability to stretch more than 5% of the amount of elongation of the stretchable, flexible closed cell membrane when applying the same tensile force. Examples of this type of material are Viton, butyl, hypalon, EPDM, and others. The arrangement of membranes (1) and (11) and (9) form a high pressure air cavity shown as reference numeral (13). The air trapped in (13) is forced into the tops of the one or more cooling air tubes and spacers shown as reference numeral (8). The tops of the one or more air tubes (8) provide a supporting/spacing function to keep air cavity (13) open between membrane (1) and membrane (9). The air forced into the tops of one or more air tubes (8) is then forced down through the one or more air tubes (8) and onto the front side of the one or more semiconductor laser diodes and lens sets shown as reference numeral (7). This forced air in addition to cooling the one or more semiconductor laser diodes and lens sets provides a cooling and drying effect on the patient's treatment area thereby enhancing comfort and preventing moisture from attenuating the laser beams. The term high pressure in this context means a varying air pressure greater than the surrounding atmospheric pressure and capable of forcing air through the one or more air tubes (8) in a manner sufficient to cool the one or more semiconductor laser diodes and lens sets.

Figure 7:
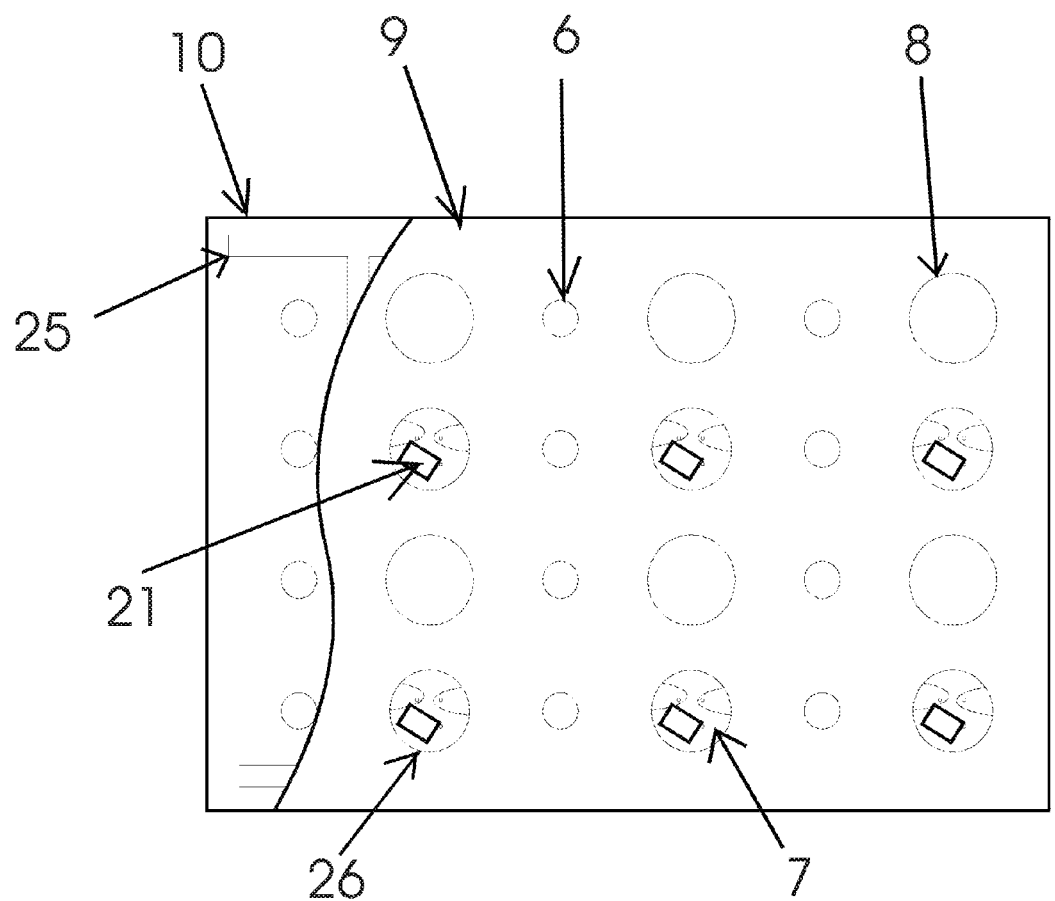
FIG. 7 is a view of the present invention looking at the electrical connection side of the semiconductor laser diode and lens sets from inside the high pressure air cavity. This view shows in detail the arrangement of the tops of the cooling air tubes and spacers, the tops of the standoff posts, the connection terminals of the semiconductor laser diode and lens sets, the automatic power control circuit electronic modules and the flexible, non-stretchable membrane (9) with holes cut directly adjacent to the semiconductor laser diode and lens sets to facilitate cooling from above.

Referring now to FIG. 7 of the drawings, reference numeral (26) refers to the one or more holes in membrane (9) directly adjacent to the pin connector side of the one or more lasers (7). Reference numeral (21) refers to the one or more automatic power control circuit electronic modules and reference numeral (25) refers to the flat braided and/or non-braided electrical conductors. The one or more holes (26) allow high pressure air to cool the one or more power control (21) and the pins of one or more laser (7) and conductors (25). This cooling effect in conjunction with the cooling effect on the front side of the one or more lasers (7) discussed above maintains the one or more lasers (7) at the optimal temperature for laser propagation.

Figure 6:
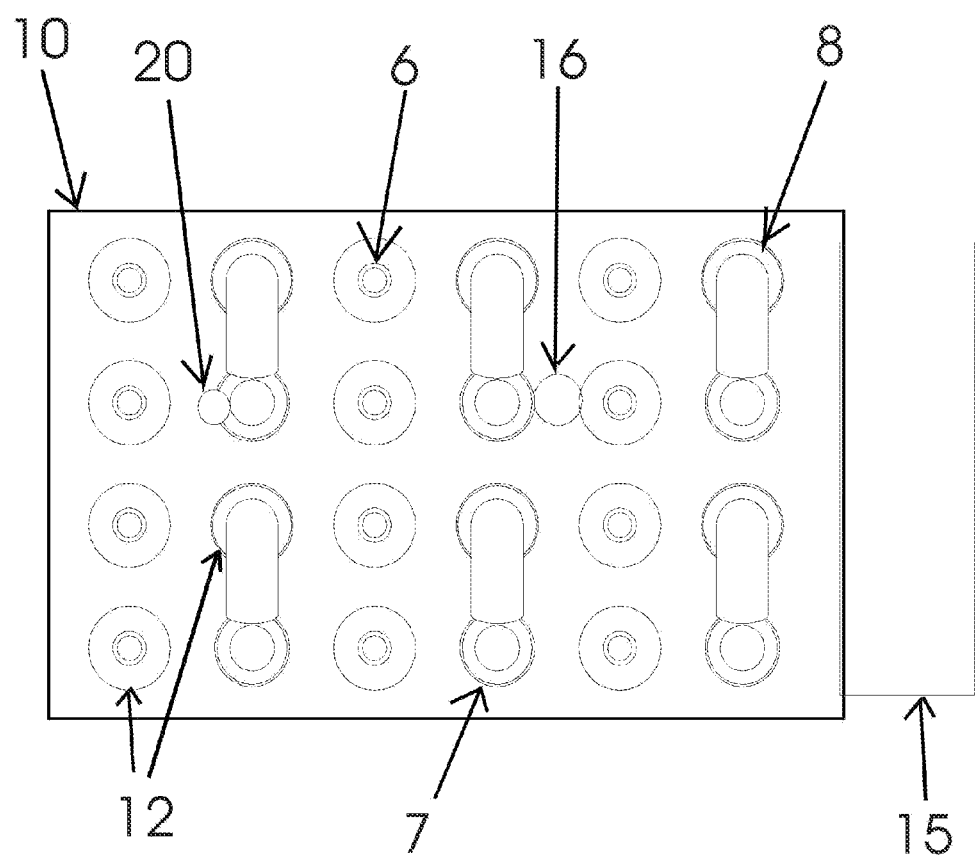
FIG. 6 is a view looking at the laser emission side of the present invention showing in detail the arrangement of the semiconductor laser diode and lens sets, the cooling air tubes and spacers, the infrared radiation sensors, the temperature sensors, the standoff posts, the flexible membrane with bonded flat braided and/or non-braided electrical conductors and the capacitive proximity sensors.

Referring now to FIG. 6 of the drawings, reference numeral (20) refers to one or more temperature sensors bonded to the radiation emitting side of the one or more lasers (7).

Referring now to FIG. 1 of the drawings, reference numeral (14) refers to an electrical cable for power and sensor data communication and reference numeral (4) refers to power supply and computer control with wireless communication.

Referring now to FIG. 1 and FIG. 5 and FIG. 6 and FIG. 7 of the drawings, the output of the one or more temperature sensors (20) is passed through power cable (14) to computer control (4) where a computer analyzes the temperature of the one or more lasers (7) and sends via power cable (14) power and timing information to regulate the speed of the one or more fans (3) thereby maintaining a constant temperature of the one or more lasers (7). The one or more lasers (7) receive power from the conductors (25) which in turn receive power from power cable (14) which in turn receives power from computer control (4).

Referring now to FIG. 1 and FIG. 6 of the drawings, reference numeral (16) refers to one or more infrared radiation sensors and reference numeral (15) refers to one or more capacitive proximity sensors. The one or more sensors (16) sense ambient light infrared radiation and infrared radiation from the patient's treatment area. The one or more sensors (15) sense a capacitive increase from the patient's treatment area when in close contact with the patient's treatment area. The one or more sensors (16) and the one or more sensors (15) send data via power cable (14) to the computer control (4) where a computer analyzes infrared radiation and the capacitance information and determines if the TLD is in close contact with the patient's treatment area. The infrared radiation must be below what is received from ambient light (high threshold) and must be equal to or greater than what is expected from the treatment area of a patient (low threshold). If the infrared radiation is equal to or greater than the low threshold and below the high threshold the computer then checks the capacitance value. If both the infrared radiation levels and the capacitance levels are within range the computer sends a signal to the touch screen computerized device with wireless communication reference numeral (5) and will allow a therapy session to begin when initiated by computerized device (5). If during the therapy session either the one or more sensors (15) or the one or more sensors (16) present data to computer control (4) which is out of range computer control (4) will send a signal to computerized device (5) and computerized device (5) will terminate the therapy session. This function ensures that laser radiation is directed onto the patient's treatment area and not in a direction that would potentially cause harm. It also protects against malicious use of the TLD. In addition to the functions described above computerized device (5) displays information to the user, communicates with the computer control (4) via wireless communication, initiates a laser therapy session, terminates a laser therapy session, maintains therapy duration timing, lets a user set therapy duration, displays to the user the elapsed time and the time left in the therapy session, displays to the user battery charge level and prohibits the initiation of a therapy session if battery charge is below a prescribed level, lets a user set laser power level, lets the user set the total therapy dosage, calculates the laser power level and therapy duration based on total therapy dosage, lets the user choose between continuous or pulsed laser operation, stores previous therapy session data and lets the user select a previously stored therapy regimen, lets a medical professional transmit a therapy regimen to the touch screen computerized device with wireless communication via the internet or cellular telephone and monitor the status of the TLD and the number of therapy sessions completed, sounds an audible signal when a therapy session is initiated, sounds an audible signal when a therapy session is terminated, waits a standard length of time after the audible signal before initiating laser power, sounds an audible alarm in the case the TLD becomes separated from the patient's treatment area, warns the user of problems encountered by the TLD, shuts the TLD down in the event of malfunction, lets the user pause the therapy session and restart the therapy session, displays a standard laser warning message about laser safety, maintains a constant wireless communication dialog with computer control (4) and in the event the communication dialog is broken computer control (4) terminates the therapy session. The communication transmission between the computerized device with wireless communication and the power supply and computer control is encrypted for security as is the transmission over the internet or cellular phone. The touch screen computerized device with wireless communication is either a made for purpose device programmed to perform the functions described above and provided with the TLD or it is an application program (computer code) loadable to a cellphone, touch screen tablet, lap top computer or a desk top computer which has been approved and certified as being capable of performing the stated functions.

Figure 4:
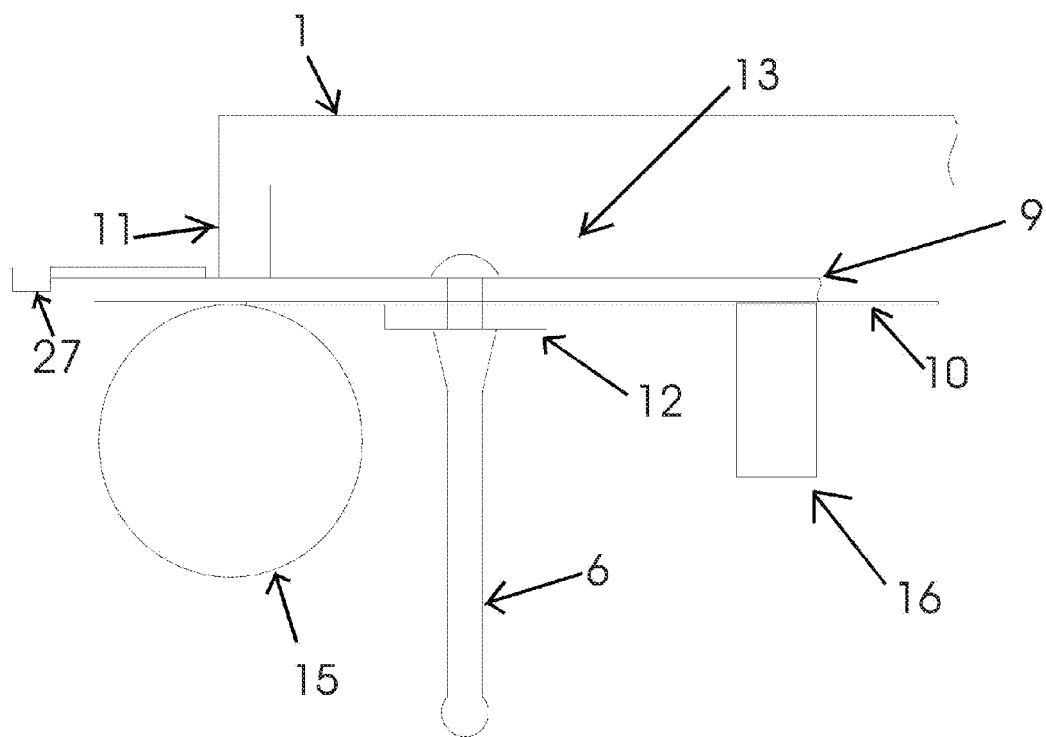
FIG. 4 is a side view of the present invention showing in detail the arrangement of the standoff posts in relation to the capacitive proximity sensors, the infrared radiation sensors and the high pressure air cavity.
Figure 10:
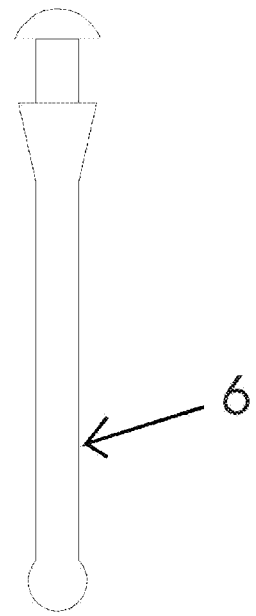
FIG. 10 is a side view of the present invention showing in detail the standoff posts.

Referring now to FIG. 4 and FIG. 5 and FIG. 10 of the drawings, reference numeral (6) refers to the one or more standoff posts. Membrane (9) is attached to flexible membrane with bonded flat braided and/or non-braided electrical conductors reference numeral (10) by means of the one or more standoff posts which penetrate and hold together membrane (9) and membrane (10). Membrane (10) can be made of polyimide, polyester, polyethylene napthalate, or polyetherimide among others. The one or more standoff posts provide, in addition to their attachment function, a separation function between the lasers (7) and the surface area to be treated on a patient. Reference numeral (12) refers to one or more flexible membrane washers which add rigidity to the standoff posts (6). The standoff posts are formed to present a small cross sectional area to the laser light so as not to block a large degree of the laser light from reaching the treatment area.

Figure 9:
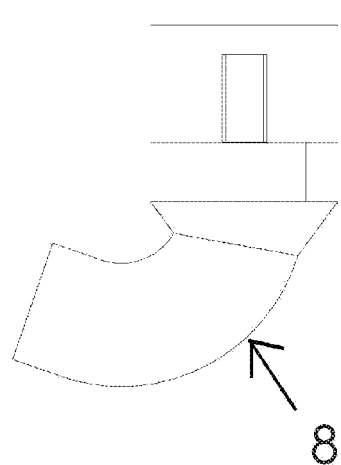
FIG. 9 is a side view of the present invention showing in detail the cooling air tubes and spacers.

Referring now to FIG. 3 and FIG. 9 of the drawings, reference numeral (12) refers to one or more flexible membrane washers which add rigidity to the one or more air tubes (8).

Figure 8:
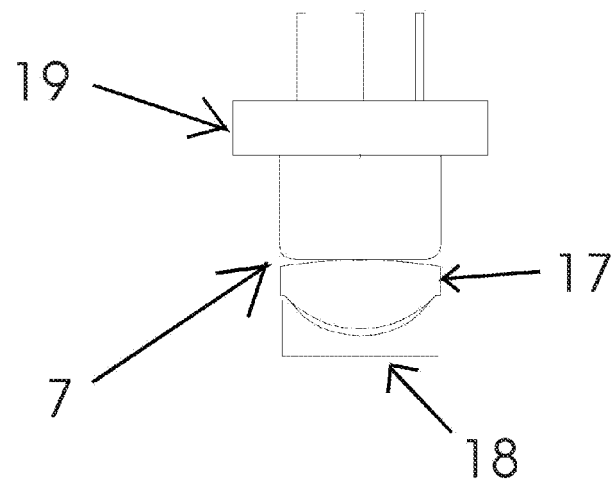
FIG. 8 is a side view of the present invention showing in detail the arrangement of the semiconductor laser diodes, the collimating lens and the plano-concave lens.
Figure 11:
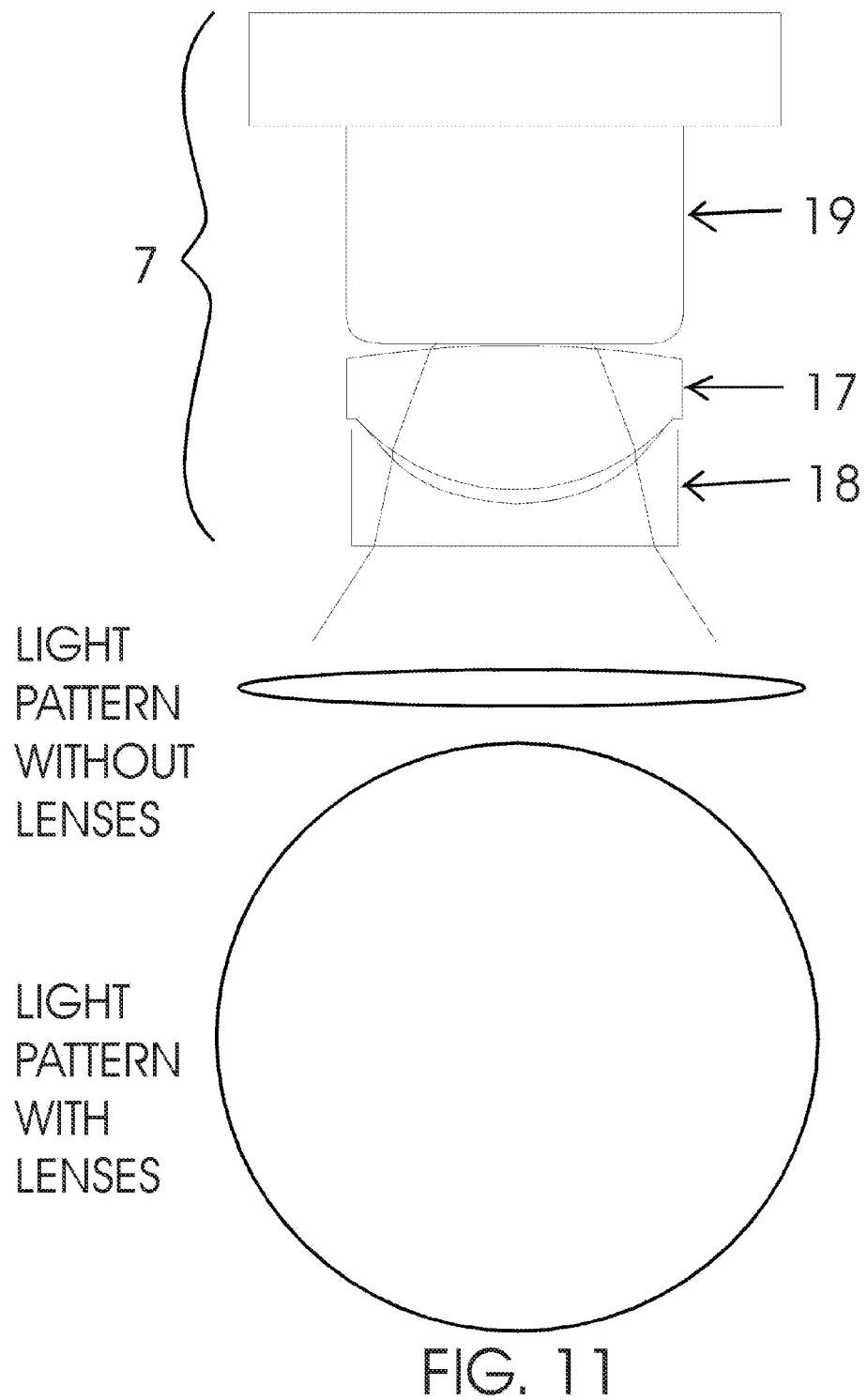
FIG. 11 is a view of the present invention showing in detail the semiconductor laser diode and lens sets collimating and then spreading the laser light of the diode. This view shows the light pattern from a laser with no lenses and laser light through both lenses.

Referring now to FIG. 8 and FIG. 11 of the drawings, reference numeral (19) refers to the one or more semiconductor laser diodes, reference numeral (17) refers to the one or more collimating lenses and reference numeral (18) refers to one or more plano-concave lenses which in combination comprise the one or more lasers (7). The light emitted by the one or more diodes (19) is in the form of an ellipse as indicated by 'LIGHT PATTERN WITHOUT LENSES' on FIG. 11. The light emitted by lasers (7) after passing through the one or more lenses (17) and (18) is in the form of a circle as indicated by 'LIGHT PATTERN WITH LENSES' on FIG. 11. This light pattern transformation is necessary to produce and even distribution of laser light radiation under each of the one or more laser (7) to affect a uniform dosage. The standoff posts (6) are formed in such a way that the distance between the lasers (7) and the patient's treatment area is optimized such that the entire treatment area is uniformly radiated with the prescribed dosage.

Figure 12:
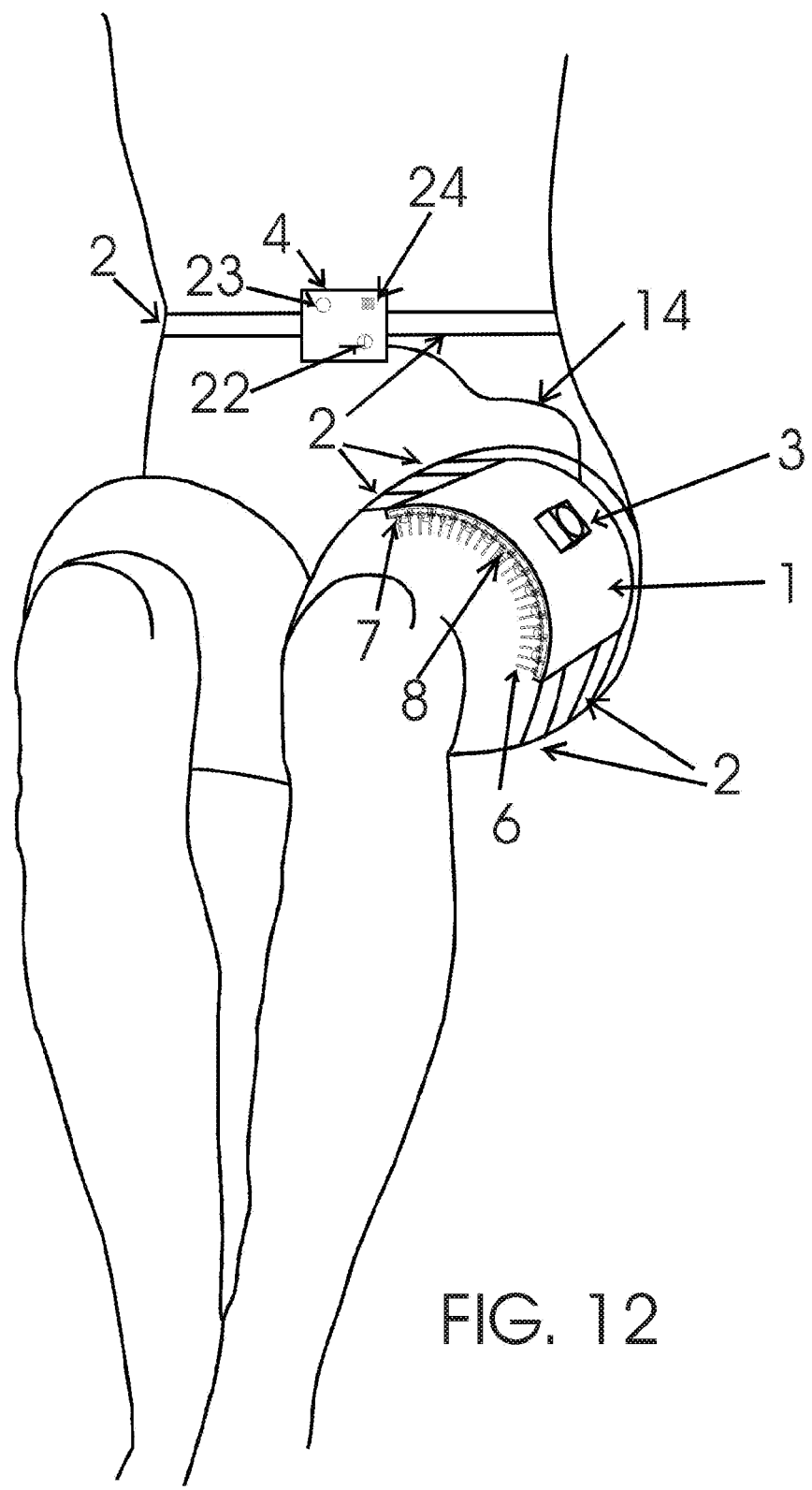
FIG. 12 is a view showing one possible embodiment of the present invention with all the major assemblies depicted in a usable arrangement on the leg of a patient.

Referring now to FIG. 1 and FIG. 3 and FIG. 12 of the drawings, reference numeral (2) refers to stretchable straps with hook and loop fasteners. The stretchable straps with hook and loop fasteners (2) enable the TLD to be fixed to a patient in a manner that allows movement of the area to be treated and movement of the patient within and without the treatment premises. The stretchable straps with hook and loop fasteners (2) are connected to the TLD with zippers, reference numeral (27), to enable quick removal for cleaning and replacement. The movement of the patient must not exceed the maximum range of the communication capability between computer control (4) and computerized device (5) or the therapy session will be terminated by computer control (4). Computer control (4) also has stretchable straps with hook and loop fasteners (2). Computer control (4) can provide power either by battery or by connection to mains power at the wall. Computer control (4) maintains the voltage and current to the semiconductor lasers within close tolerances to ensure the correct laser power and dosage levels. Computer control (4) contains a key lock reference numeral (22) which provides security against unauthorized use, a laser radiation full duration indicator light reference numeral (23) which provides laser-on indication and a laser radiation momentary at start audible signal device reference numeral (24) which provides an indication of the beginning of a therapy session.

Figure 13:
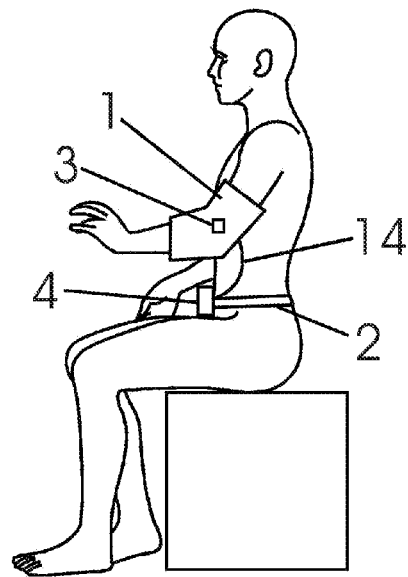
FIG. 13 is a view showing a second possible embodiment of the present invention depicted in a usable arrangement on the elbow of a patient.
Figure 14:
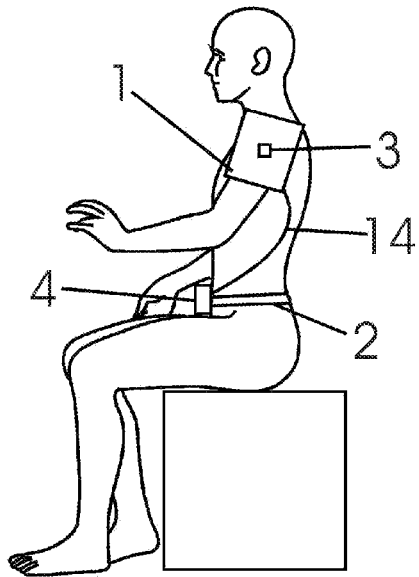
FIG. 14 is a view showing a third possible embodiment of the present invention depicted in a usable arrangement on the shoulder of a patient.
Figure 15:
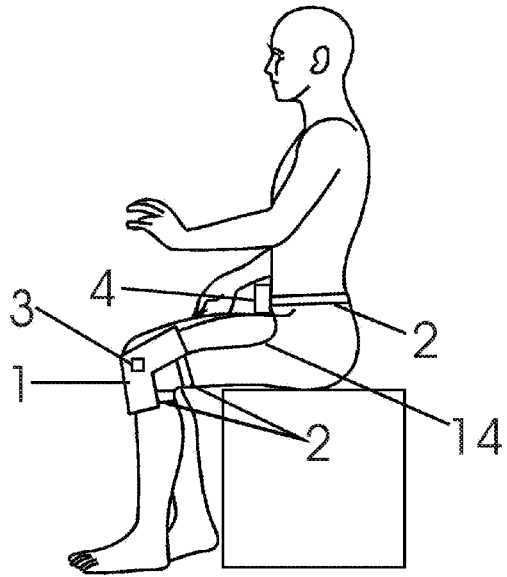
FIG. 15 is a view showing a fourth possible embodiment of the present invention depicted in a usable arrangement on the knee of a patient.
Figure 16:
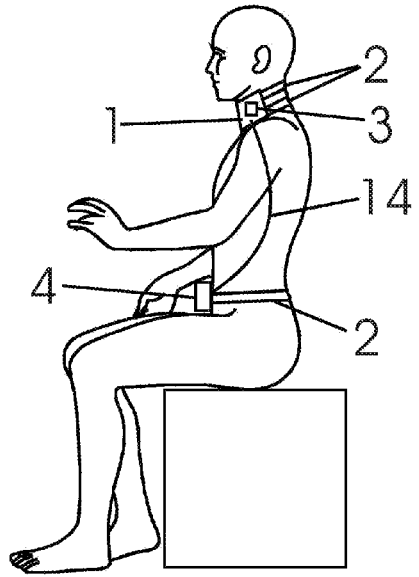
FIG. 16 is a view showing a fifth possible embodiment of the present invention depicted in a usable arrangement on the neck of a patient.

Referring now to FIG. 13 and FIG. 14 and FIG. 15 and FIG. 16 of the drawings show additional possible embodiments of the present invention but do not limit the potential embodiments that could be created using the same technology. FIG. 13 shows an embodiment designed for the elbow. FIG. 14 shows an embodiment designed for the shoulder. FIG. 15 shows an embodiment designed for the knee. FIG. 16 shows an embodiment designed for the neck. Additional embodiments could include but are not limited to the lower back, the ankle, the top of the foot, the bottom of the foot, the head, the hand, the buttocks, the lower leg, the face, etc.

Referring to FIG. 17 of the drawings it is shown that physiological activity affected by laser light energy is not uniform but is greater in certain wavelengths than others.

What is claimed is:

1. A therapeutic laser device (laser device) comprising:
a plurality of semiconductor laser diodes arranged in a two dimensional array bonded to a first flexible membrane (10) with bonded flat braided and/or non-braided electrical conductors, each semiconductor laser diode positioned for emitting coherent electromagnetic radiation in the range of 380 nm to 1,400 nm in a direction perpendicular to the first flexible membrane (10);
a second flexible, non-stretchable membrane (9) attached to the first flexible membrane (10), on the side opposite to that of the plurality of semiconductor laser diodes, by a plurality of standoff posts penetrating both membranes and affecting a union between the first flexible membrane (10) and the second flexible, non-stretchable membrane (9), wherein the plurality of standoff posts are configured to contact a treatment area and thereby provide a predetermined distance between the treatment area and the plurality of semiconductor laser diodes;
a first narrow, stretchable, flexible closed cell membrane (11);
one or more high pressure fans with speed control and air filters;
a second stretchable, flexible closed cell membrane;
one or more capacitive proximity sensors which detect an increase of capacitance when in close contact with a patient's treatment area;
one or more infrared radiation sensors which detect infrared radiation from ambient light and infrared radiation from the patient's treatment area;
one or more temperature sensors which detect the temperature of the plurality of semiconductor laser diodes;
a plurality of cooling air tubes and spacers each associated with one of the plurality of semiconductor laser diodes;
a plurality of automatic power control circuit electronic modules each associated with one of the plurality of semiconductor laser diodes.

2. The laser device of claim 1 wherein each of the plurality of laser diodes is fitted with a collimating lens followed by a plano-concave lens to affect a circular laser radiation pattern thereby providing an even distribution of radiation over a treatment area.

3. The laser device of claim 1 wherein the plurality of standoff posts are configured:
to ensure a uniform distance between the plurality of laser diodes and a patient's treatment area;
to ensure an optimum distance between the plurality of laser diodes and a patient's treatment area thereby producing a uniform dosage of laser radiation;
with a bulbous end configured to contact a patient's treatment area;
to provide a union between the first flexible membrane (10) and the second flexible, non-stretchable membrane (9) a by means of protrusions and fillets on the standoff posts allowing a small slip to occur between the first flexible membrane (10) and the second flexible, non-stretchable membrane (9) when under stress due to flexure of the laser device;
to accept flexible membrane washers on the side of the plurality of laser diodes thereby providing rigidity to the standoff posts;
to present a small cross sectional area to the laser light so as not to block a large degree of the laser light from reaching the treatment area.

4. The laser device of claim 1 wherein power to the plurality of laser diodes is provided by the flat braided and/or non-braided electrical conductors which in turn receive power from an electrical cable for power and sensor data communication which in turn receives its power from a power supply and computer control with wireless communication.

5. The laser device of claim 1 wherein the second flexible, non-stretchable membrane (9) is bonded to said first narrow, stretchable, flexible closed cell membrane (11) which in turn is bonded to a stretchable, flexible closed cell membrane (1) thereby forming a high pressure air cavity.

6. The laser device of claim 4 wherein the one or more capacitive proximity sensors, the one or more infrared radiation sensors and the one or more temperature sensors send their data through the electrical cable for power and sensor data communication to the power supply and computer control with wireless communication.

7. The laser device of claim 5 wherein each of the plurality of cooling air tubes and spacers are configured to:

direct high pressure air from the high pressure air cavity through the first flexible membrane and the second flexible, non-stretchable membrane (9) and onto the radiation emitting side of each of the plurality of semiconductor lasers thereby cooling the plurality of semiconductor lasers;

directs high pressure air from the high pressure air cavity through the first flexible membrane and the second flexible, non-stretchable membrane (9) and onto the radiation emitting side of each of the plurality of semiconductor lasers thereby providing a cooling and drying effect on the patient's treatment area thereby enhancing comfort and preventing moisture from attenuating the laser beams;

provide a supporting/spacing function to keep the high pressure air cavity open between the second stretchable, flexible closed cell membrane (1) and the second flexible, non-stretchable membrane (9);

and be formed in such a way that the high pressure air enters the top of the cooling air tubes and spacers through one or more ports.

8. The laser device of claim 7 wherein the second flexible, non-stretchable membrane (9) has one or more holes cut into the membrane directly adjacent to the one or more semiconductor lasers on the side of the laser opposite to the radiation emitting side allowing high pressure air to cool the one or more automatic power control circuit electronic modules, the flat braided and/or non-braided electrical conductors and the one or more semiconductor lasers, which in conjunction with the cooling effect on the radiation emitting side of the one or more semiconductor lasers provided by the cooling air tubes and spacers, maintains the one or more semiconductor lasers at the optimal temperature for laser radiation propagation.

9. The laser device of claim 1 has attached to it, by means of zippers, stretchable straps with hook and loop fasteners enabling the laser device to be fixed to a patient in a manner that allows movement of the area to be treated and movement of the patient.

10. The laser device of claim 4 wherein the power supply and computer control with wireless communication analyzes the output of the one or more temperature sensors and sends power and timing information through the electrical cable for power and sensor data communication to regulate the speed of the one or more high pressure fans with speed control and air filters thereby maintaining a constant temperature of the plurality of lasers.

11. The laser device of claim 4 wherein the power supply and computer control with wireless communication analyzes:

the output of the one or more infrared radiation sensors to determine if the infrared radiation level is below what is expected from ambient light (high threshold) and equal to or greater than what is expected from the treatment area of a patient (low threshold);

the output of the one or more capacitive proximity sensors to determine if the capacitive value is that which is expected when in close contact with a patient's treatment area;

and prevents laser radiation from being energized if either the infrared radiation sensor data or the capacitive sensor data is out of range thereby ensuring that laser radiation is directed onto the patient's treatment area and not in a direction that would potentially cause harm.

12. The laser device of claim 5, wherein the second stretchable, flexible closed cell membrane (1) has bonded to it said one or more high pressure fans with speed control and air filters which produce the high pressure air in the high pressure air cavity.

13. The laser device of claim 11 wherein the power supply and computer control with wireless communication has built into it:

a laser radiation full duration indicator light to provide a visible indication of the presence of laser radiation;

a laser radiation momentary at start audible signal device to indicate the beginning of laser radiation;

a key lock to prevent either unauthorized use or malicious use of the laser device;

the power supply and computer control with wireless communication further configured to:

provide power by means of rechargeable batteries or through connection to mains power at the wall;

maintain the voltage and current to the semiconductor lasers within close tolerances to ensure the correct laser power and dosage levels;

communicate wirelessly with another computerized device using encryption;

turn off the laser radiation in the case that a computerized device with which it is communicating stops the communication dialog.

14. The laser device of claim 11 has attached to it, by means of zippers, stretchable straps with hook and loop fasteners enabling the apparatus to be fixed to a patient in a manner that allows movement of the area to be treated and movement of the patient.

* * * * *